United States Patent [19]
Begue et al.

[11] Patent Number: 5,091,429
[45] Date of Patent: Feb. 25, 1992

[54] DERIVATIVES OF 4-AMINO-1-TRIFLUOROMETHYLTETRA-LINES THEIR PREPARATION AND THEIR THERAPEUTIC APPLICATION

[75] Inventors: Jean-Pierre Begue; Micheline Charpentiermorize; Danièle Bonnet Delpon, all of Paris; Huguette Gilbert-Semon, Chartres Cedex, all of France

[73] Assignee: Laboratoires Lucien, Colombes, France

[21] Appl. No.: 391,582

[22] PCT Filed: Nov. 24, 1988

[86] PCT No.: PCT/FR88/00575
§ 371 Date: Jul. 24, 1989
§ 102(e) Date: Jul. 24, 1989

[87] PCT Pub. No.: WO89/04820
PCT Pub. Date: Jun. 1, 1989

[30] Foreign Application Priority Data
Nov. 26, 1987 [FR] France ................ 87 16436

[51] Int. Cl.$^5$ ................ A61K 31/495; A61K 31/135; C07D 295/08; C07C 87/40
[52] U.S. Cl. .................... 514/255; 544/401; 544/403
[58] Field of Search ............ 544/401, 403; 514/255

[56] References Cited

U.S. PATENT DOCUMENTS 4,536,518 8/1985 Welch, Jr. et al. ............ 514/555
4,556,676 12/1985 Welch, Jr. et al. ............ 514/555

FOREIGN PATENT DOCUMENTS 1420472 1/1976 United Kingdom .

Primary Examiner—Cecilia Shen
Attorney, Agent, or Firm—Dennison, Meserole, Pollack & Scheiner

[57] ABSTRACT

Derivatives of 4-amino-1-trifluoromethyltetralines of general formula:

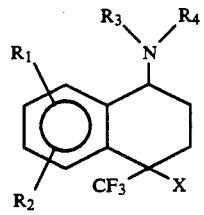

wherein:

X represents an aromatic nucleus, namely phenyl, naphthyl, or thienyl able to carry one to two substituents chosen from halogeno, hydroxy, $C_1$ to $C_8$ alkoxy or trifluoromethyl;

$R_1$ represents a hydrogen atom or a halogen, a hydroxy group, a $C_1$ to $C_8$ alkoxy group, in one of positions 5, 6 or 7, or even a methylenedioxy group in positions 5 and 6 or 6 and 7;

$R_2$ represents a hydrogen atom or a halogen, a hydroxy group, a $C_1$ to $C_8$ alkoxy group in one of the other positions 5, 6 or 7, and $R_3$ and $R_4$ each represent a hydrogen atom, a methyl group or a linear or branched $C_1$ to $C_n$ alkyl group, n being 2 or more, possibly halogenated, hydroxylated or aminated, or $R_3$ and $R_4$ together with the nitrogen atom to which they are linked form a saturated heterocyclic compound, possibly substituted, with five or six atoms of which one or two are heteroatoms chosen from nitrogen, oxygen or sulfur.

17 Claims, 1 Drawing Sheet

DERIVATIVES OF 4-AMINO-1-TRIFLUOROMETHYLTETRALINES THEIR PREPARATION AND THEIR THERAPEUTIC APPLICATION

BACKGROUND OF THE INVENTION

The present invention relates to derivatives of 4-amino-1-trifluoromethyltetraline, the process for their preparation and their therapeutic application.

DESCRIPTION OF THE PRIOR ART

Aminotetralines having an antidepressant activity have already been described, this is the case for example, in European patent applications N° 30081 and 28901.

These actively studied compounds do not appear to have the unwanted side effects, particularly at the cardiovascular level, of other antidepressants, such as the tricyclic compounds.

SUMMARY OF THE INVENTION

The applicant has now found aminotetralines, and acid addition salts thereof, having a trifluoromethyl group on an alicyclic carbon in place of a hydrogen atom and having antidepressant and analgesic activities.

Introduction of a trifluoromethyl group into a molecule increases its lipophilic properties and reinforces or creates pharmacological activity by facilitating cellular penetration and crossing of the hematoencephalic barrier.

But known techniques of trifluoromethylation of the aliphatic carbon still present enormous difficulties.

The applicant has developed new processes for the preparation of trifluoromethylated tetralines useful, in particular, in the synthesis of trifluoromethylated aminotetralines.

Consequently, the object of the present invention is the derivatives of 4-amino-1-trifluoromethyltetralines of general formula:

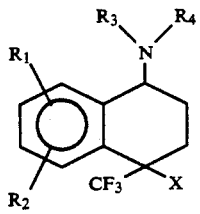

[I]

wherein:
X represents an aromatic nucleus, namely phenyl, naphthyl α or β thienyl able to carry one to two substituents chosen from halogeno, hydroxy, $C_1$ to $C_8$ alkoxy, trifluoromethyl;

$R_1$ represents a hydrogen atom or a halogen, a hydroxy group, a $C_1$ to $C_8$ alkoxy group, in one of positions 5, 6 or 7, or even a methylenedioxy group in positions 5 and 6 or 6 and 7;

$R_2$ represents a hydrogen or halogen atom, a hydroxy group, a $C_1$ to $C_8$ alkoxy group in one of the other positions 5, 6 or 7, and $R_3$ and $R_4$ each represents a hydrogen atom, a linear or branched $C_1$ to $C_n$ alkyl group, n being 2 or more, possibly halogenated, hydroxylated or aminated, or $R_3$ and $R_4$ together with the nitrogen atom to which they are linked form a saturated heterocyclic compound, possibly substituted, with five or six atoms of which one or two are heteroatoms chosen from nitrogen, oxygen or sulfur.

Among the compounds of formula I defined hereinabove, a preferred class of compounds comprises the derivatives wherein X is a phenyl ring able to carry one to two substituents chosen from halogeno, hydroxy, $C_1$ to $C_8$ alkoxy or trifluoromethyl.

The compounds of formula I wherein X represents a phenyl ring carrying 1 to 2 halogen atoms appear to be particularly advantageous.

The compounds of formula I have an amine function on carbon number 4; depending on the nature of $R_3$ and $R_4$, the compounds of the invention can thus be primary amines, secondary amines or tertiary amines; the following can be given as examples:

primary amines in which $R_3$ and $R_4$ represent a hydrogen atom;

secondary amines in which $R_3$ represents a hydrogen atom and $R_4$ represents a methyl group or a group of formula $—(CH_2)_n—OH$ in which n is 2 or more;

tertiary amines in which $R_3$ and $R_4$ each represent a methyl group or $R_3$ and $R_4$ together with the nitrogen atom to which they are linked form a group of formula:

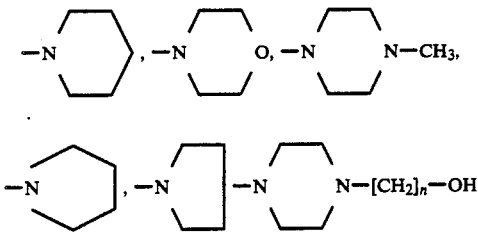

wherein n=2 or more.

As halogens, chlorine and fluorine are particularly preferred.

The following derivatives and their hydrochlorates, given in the tables below, can be cited as non limiting examples of compounds of formula I which are useful according to the present invention.

The syntheses described hereinafter lead to a mixture of two racemic diastereoisomers a and b which can be separated by conventional chromatography or fractional crystallization processes and each diastereoisomer is likely to be divided into two optic isomers.

All these compounds fall within the scope of the present invention.

The compounds of formula I which can form salts also constitute part of the invention. Conventionally formed salts comprise acid addition salts which are formed with various mineral and organic acids, for example, halohydrates, sulfates, nitrates, tartrates, mandelates, acetates, succinates, benzenesulfonates.

The compounds of the present invention can be prepared using the various processes described hereinafter.

The compounds of formula I can be prepared from derivatives of 1-aryl-1-trifluoromethyltetralines having the following formula:

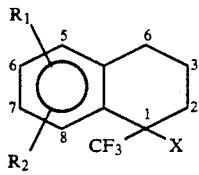

wherein $R_1$, $R_2$ and X have the same meaning as in formula I.

The derivatives of 1-aryl-1-trifluoromethyltetralines (II) can, if the case arises, be prepared by solvolysis of the corresponding derivatives (known) of 5-aryl-1,1,1-trifluoro-pentan-2-ol of formula:

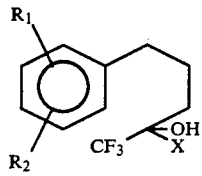

wherein $R_1$, $R_2$ and X have the same meaning as in formula I.

A first process for the preparation of a compound of formula I consists in halogenating a derivative of 1-aryl-1-trifluoromethyltetraline of formula II wherein $R_1$, $R_2$ and X have the same meaning as in formula I to obtain the corresponding halide of formula:

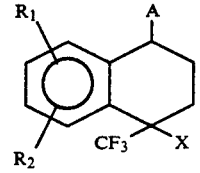

| Compound No | $R_2$ | $R_1$ | $R_3$ | $R_4$ | X |
|---|---|---|---|---|---|
| 1 | H | H | \-N(piperidine) | | phenyl |
| 2 | H | H | —CH₃ | —CH₃ | phenyl |
| 3 | H | H | H | —CH₃ | phenyl |
| 4 | H | H | —N(piperazine)NCH₂CH₂OH | | phenyl |
| 5 | H | OCH₃ in position 7 | H | CH₃ | phenyl |
| 6 | H | —OCH₃ in position 7 | —N(piperazine)NCH₂CH₂OH | | phenyl |
| 7 | H | methylenedioxy in position 6 and 7 | H | CH₃ | 4-Cl-phenyl |
| 8 | H | —OCH₃ in position 7 | CH₃ | CH₃ | 3-Cl-phenyl |

-continued

| Compound No | R₂ | R₁ | R₃ | R₄ | X |
|---|---|---|---|---|---|
| 9 | H | Cl in position 7 | —N(piperazine)N—CH₂—CH₂—OH | | 2-chlorophenyl |
| 10 | Cl in position 6 | Cl in position 7 | H | H | 4-chlorophenyl |
| 11 | H | —OCH₃ in position 7 | H | CH₃ | 2-chlorophenyl |
| 12 | H | H | H | —CH₂—CH₂—OH | phenyl |
| 13 | H | H | —N(piperazine)N—CH₂—CH₂—OH | | 4-chlorophenyl |
| 14 | H | H | H | CH₃ | 3,4-dichlorophenyl |
| 15 | H | —OCH₃ in position 7 | H | —CH₃ | 2,3-dichlorophenyl |
| 16 | H | H | CH₃ | —CH₂—CH₂—OH | 3,5-dichlorophenyl |
| 17 | H | Cl in position 7 | —N(piperazine)N—CH₂—CH₂OH | | 2,6-dichlorophenyl |
| 18 | Cl in position 6 | OCH₃ in position 7 | H | CH₃ | 3,4-dichlorophenyl |
| 19 | H | H | —N(piperazine)N—CH₂—CH₂—OH | | 3,4-dichlorophenyl | wherein R₁, R₂ and X have the same meaning as in formula I and A represents a halogen, to be reacted over the latter an amine of formula:

IV wherein $R_3$ and $R_4$ have the same meaning as in formula I to obtain a mixture of the two diastereoisomers of the corresponding compound of formula I.

The halogenation reaction of a derivative of 1-aryl-1-trifluoromethyl tetraline (II), according to the present process, is advantageously carried out with a halogenosuccinimide under reflux with $CCl_4$ and in the presence of benzoyl peroxide.

The reaction between the halide of formula III and the amine of formula IV according to the present process is preferentially carried out in toluenic solution for over 24 hours and at room temperature.

The compounds of formula I wherein $R_3$ or $R_4$, or $R_3$ and $R_4$ represent a hydrogen atom can also be prepared by a second process which consists in oxidizing a derivative of formula II to obtain the corresponding tetralone of formula

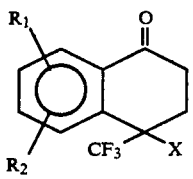

wherein $R_1$, $R_2$ and X have the same meaning as in formula I, by reacting the latter with an amine of formula IV wherein $R_3$ or $R_4$, or $R_3$ and $R_4$ represent a hydrogen atom, to obtain a nitrogenated residue which is reduced by a hydride to obtain the corresponding compound of formula I, which is a primary amine ($R_3$ or $R_4$ represent a hydrogen atom) or a secondary amine ($R_3$ or $R_4$ represent a hydrogen atom).

When tetralone (V) is reacted with an amine of formula IV wherein $R_3$ or $R_4$ represent a hydrogen atom, a nitrogenated residue is obtained which is an imine, and to reduce the latter, $Li Al H_4$ is preferably used as a hydride to obtain a compound of formula I which is a secondary amine.

When tetralone (V) is reacted with an amine of formula IV wherein $R_3$ or $R_4$ represent a hydrogen atom, a nitrogenated residue is obtained which is an oxime, and to reduce the latter, $NaBH_4$ is preferably used as a hydride to obtain a compound of formula I which is a primary amine.

PRESENTATION OF DRAWINGS

The examples and figures hereinafter are given as illustrations of the process for the preparation of compounds according to the present invention:

DESCRIPTION OF THE PREFERRED EMBODIMENTS OF THE INVENTION

EXAMPLE 1

Figure 1:
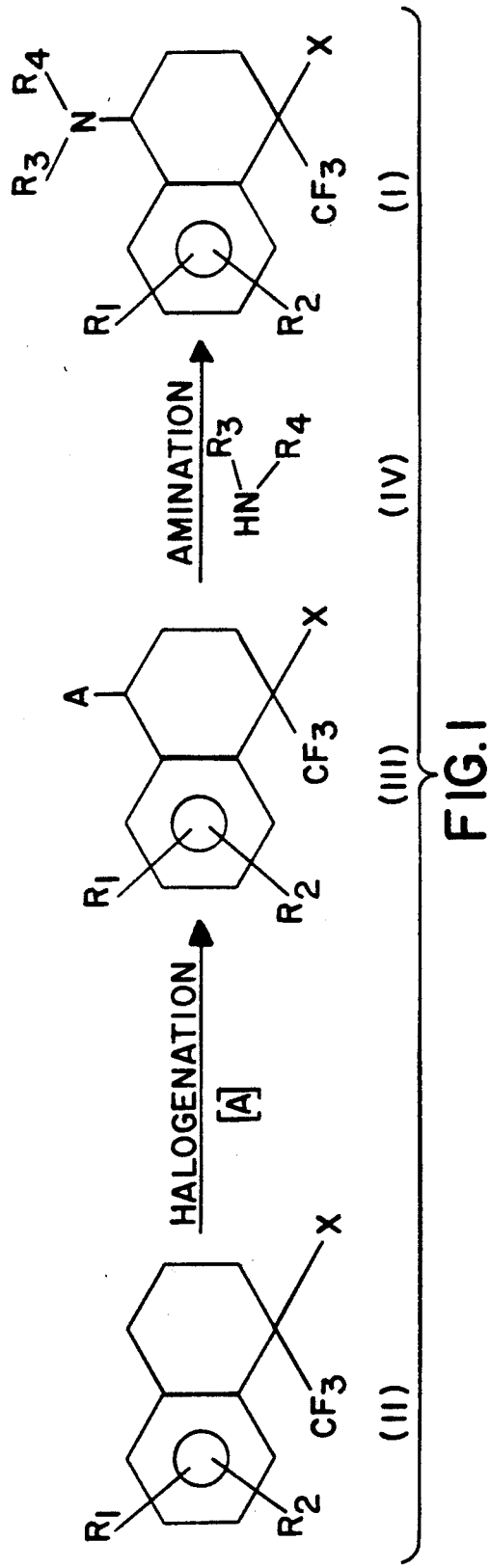
FIG. 1 represents the general reactional diagram according to the first process for the preparation of compounds of formula I.

Preparation of compound N° 4 through the intermediate of the corresponding halide (FIG. 1).

($R_1$ and $R_2$ each represent a hydrogen atom, X represents a phenyl ring and $R_3$ and $R_4$ together with the nitrogen atom to which they are linked form a group of formula

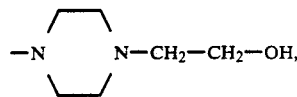

in formula I).

750 mg of benzoyl peroxide and 9.79 g of N-Bromosuccinimide. ($5.5.10^{-2}$ mole) are added to a solution of 13.8 g of 1-trifluoromethyl-1-phenyl-1,2,3,4-tetrahydronaphthalene ($5.10^{-2}$ mole) in 150 ml of $CCl_4$. After 3 hours of reflux under magnetic stirring, the solution is cooled down and filtered, then concentrated under vacuum. The residue is taken up with pentane and quickly filtered on 25 g of florisil. After evaporation of the solvent, 16.6 g of crude bromide is obtained which is used as it is; the yield of the halogenation reaction is 88%.

This bromide dissolved in 200 ml of toluene is left in contact with 18 g (3 equivalents) of piperizine ethanol for six days. The reaction mixture is extracted three times with 20% hydrochloric acid. The combined acid fractions are extracted with ether, filtered on paper and treated with 20% NaOH. The base thus liberated is extracted by a $CH_2Cl_2$-$Et_2O$ mixture; after several washings with water to eliminate excess piperizine ethanol, the solution is dried ($Na_2SO_4$) then concentrated under vacuum.

14.2 g of a 55/45 mixture of the two diastereoisomers 4a and 4b of amino-trifluoromethyl-tetraline N° 4 are thus obtained. The yield of the reaction is 70%. To separate these two diastereoisomers, the 14.2 g of crude amino-trifluoromethyl-tetraline N° 4 are dissolved with heating in about 200 ml of pentane.

After separation of the insoluble fraction, diastereoisomer 4a crystallizes out slowly.

6.1 g of pure compound 4a are thus isolated. After evaporation of the solvent, the mother liquors give 7.9 g of about a 20–80 mixture of diastereoisomers 4a and 4b. This mixture, taken up by ether, is treated with an ethereal hydrochloric gas solution. The hydrochlorate crystals thus formed are separated away from humidity and drawn off under vacuum in a rotary evaporator for two hours at 80° C. By crystallizing in absolute ethanol, 4.1 g of the hydrochlorate of pure diastereoisomer 4b are separated.

It is also possible to separate the two diastereoisomers 4a and 4b by flash-chromatography ($SiO_2$; eluent: $EtO_2$-MeOH 99-1); diastereoisomer N° 4a is eluted first. Characterization of diastereoisomer N° 4a:

Melting point: M=125.5° ($Et_2O$-Hexane).

Analysis: empirical formula $C_{23}H_{27}ON_2F_3$; molecular weight 404: Found % C:68.23 H:6.60 N:7.12. Calc % C:68.32 H:6.68 N:6.93.

NMR (CD $Cl_3$): δ (ppm):
$^1H$: 7.9–7.0 (m, 9H, 20); 3.90 (d. of d. $J_A$=11.8 Hz, $J_B$=5.6 Hz, N-CH); 3.58 (t,2H, $CH_2OH$); 2.6–2.0 (m, 14H, $CH_2$).

$^{19}F$: −66.7 (ref. $CFCl_3$).

$^{13}C$: 141.0, 139.5, 134.7 (quaternary arom.), 129.6–126.7 (arom.), 128.3 (q,J=284.7 Hz, $CF_3$), 62.6, 59.4 ($CH_2$—$CH_2$—OH), 57.7 ($C_4$), 53.5, 47.8 (4$CH_2$), 31.6 (q,J=2.2 Hz, $C_2$) 15.9 ($C_3$).

Characterization of the hydrochlorate of diastereoisomer N° 4a:

Melting point MP: 217.5° C. (ethanol).

Analysis: empirical formula $C_{23}H_{29}Cl_2ON_2F_3$; molecular weight 477: Found % C:57.90 H:6.16 N:5.86. Calc % C:57.86 H:6.08 N:5.87.

Characterization of diastereoisomer N° 4b:

Melting point: noncrystallized.

Analysis: identical to that of compound 4b.

NMR (CD Cl$_3$): δ (ppm):

$^1$H: 7.9-7.0 (m, 9H, 20),3.77 (t,$J_A$=6.5 Hz, $J_B$=6.5 Hz, 1H, N—CH) 3.61 (t,2H, CH$_2$OH), 2.6-2.0 (m, 14H, CH$_2$).

$^{19}$F: −65.0 (ref. CFCl$_3$).

$^{13}$C: 142.6, 139.4, 135.6 (quaternary arom.), 130.4-126.7 (arom.), 128.1 (q,J=285 Hz, CF$_3$), 61.2, 59.6 (CH$_2$—CH$_2$—OH), 57.8 (C$_4$), 53.6 (q,J=23 Hz, C$_1$), 53.7, 48.7 (4CH$_2$), 32.6 (q,J=2 Hz, C$_2$), 17.9 (C$_3$).

Characterization of the hydrochlorate of diastereoisomer N° 4b:

Melting point Mp: 201° C. (EtOH).

Analysis: empirical formula $C_{23}H_{29}Cl_2N_2OF_3$; molecular weight 477: Found % C:57.9 H:6.16 N:5.86. Calc % C:57.86 H:6.08 N:5.87.

EXAMPLE 2

Figure 2:
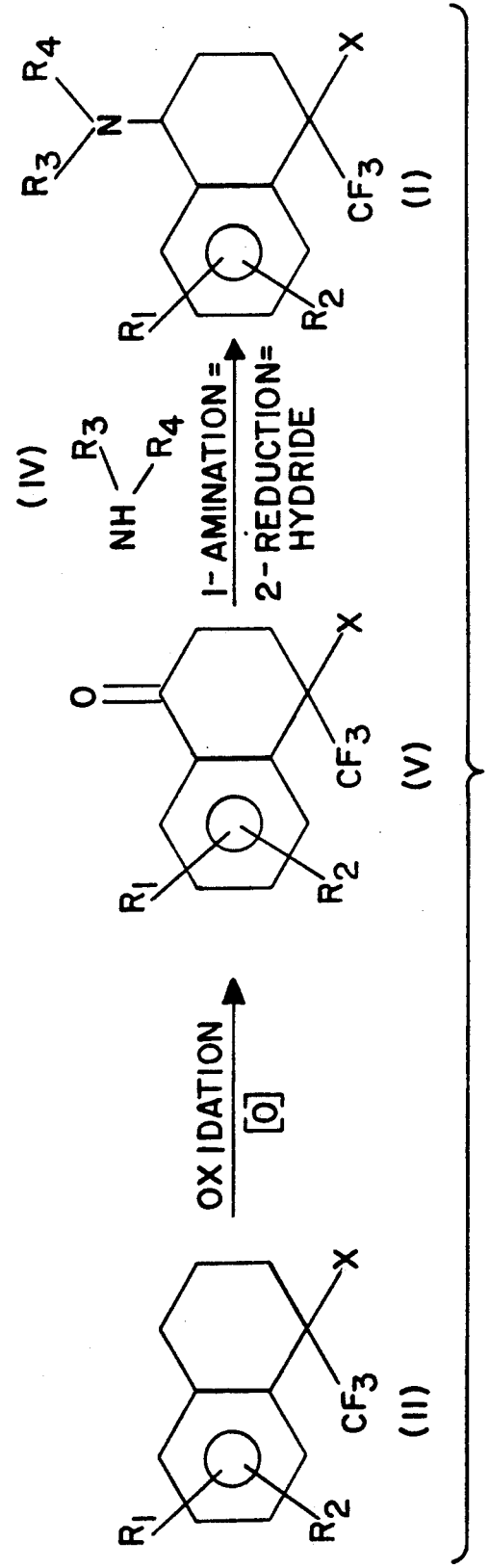
FIG. 2 represents the general reactional diagram according to the second process for the preparation of compounds of formula I wherein $R_3$ or $R_4$, or $R_3$ and $R_4$ represent a hydrogen atom.

Preparation of compound N° 5 through the intermediate of the corresponding tetralone (FIG. 2)

($R_1$ and $R_3$ each represent a hydrogen atom, X represents a phenyl group, $R_1$ represents a methoxy group in position 7 and $R_4$ represents a methyl group, in formula I).

15.3 g (5.10$^2$ mole) of 1-trifluoromethyl-1-phenyl-7-methoxy-1,2,3,4-tetrahydronaphthalene are placed under reflux for 2 hours in 150 ml of acetonitrile and 150 ml of water in the presence of 12 g of copper sulfate and 25 g of potassium peroxydisulfate. After extraction by CH$_2$Cl$_2$, washing to neutrality, the dried solution is concentrated under vacuum. The residue is filtered on a silica gel column (pentane-Et$_2$O: 9/1). After evaporation of the solvent, 13.5 g of the crystallized tetralone are isolated. The yield of the oxidation reaction is 85%. To a solution of 8 g (2.5·10$^{-2}$ mole) of tetralone in 100 ml of toluene cooled at −20° C., 7 ml of monomethylene, then 2.34 g (1.25·10$^{-2}$ mole) of TiCl$_4$ are added, with continuous stirring. The reaction is left to return to room temperature. After 17 h, the reaction mixture is hydrolyzed and quickly extracted with ether. After washing to neutrality, the solution is dried (Na$_2$SO$_4$), then concentrated under vacuum. The residue obtained is taken up with 80 ml of methanol, to which 906 mg of NaBH$_4$ is added in small amounts. After 90 minutes, the methanol is partly evaporated under vacuum; the residue, taken up with water, is extracted with ether. The neutral products are separated by passage in an acid medium (10% HCl). The base, released by 20% soda, is extracted with ether. After drying (Na$_2$SO$_4$), the solution is concentrated under vacuum. One of the two diastereoisomers of amino-trifluoromethyl tetraline N° 5b.

Characterization of diastereoisomer N° 5b:

Melting point: M=115.9° C.

Analysis: empirical formula $C_{19}H_{21}NF_3ClO$; molecular weight 371.5: Found % C:61.88 H:5.79. Calc % C:61.37 H:5.69.

NMR (CD Cl$_3$): δ (ppm):

$^1$H: 7.1 (O), 3.7 (m, 1H, N—CH), 3.77 (s, 3H, OCH$_3$), 2.3 (s, 4H, CH$_2$).

$^{19}$F: −66.0 (ref. CFCl$_3$).

$^{13}$C: 158.2 (C$_7$), 142.1, 135.6, 133.3 (quaternary arom.) 131.2 to 127.1 (arom.), 114.7 (C$_8$), 114.3 (C$_6$), 56.8 (C$_4$),55.2 (OCH$_3$), 54.2 (q,J=23.7 Hz, C$_1$), 35.5 (CH$_3$), 31.4 (C$_2$), 23.9 (C$_3$).

Characterization of the hydrochlorate of diastereoisomer N° 5b:

Melting point MP: 226.5° C. (EtOH).

Analysis: empirical formula $C_{19}H_{21}NF_3ClO$; molecular weight 371.8; Found % C:60.88 H:5.79 N:3.81. Calc % C:61.37 H:5.69 N:3.77.

TOXICO-PHARMACOLOGICAL STUDY

The pharmacological study of the compounds of the invention allowed detection of an analgesic and antidepressant effect.

The pharmacological tests carried out are as follows:

I. Acute toxicity

Determination of mortality in the mouse is observed following unique administration by oral route of increasing doses of the compounds to be tested. The LD$_{100}$ for all the compounds studied is greater or equal to 400 mg/kg, for example, that of compound 4a is greater than or equal to 800 mg/kg.

The LD$_0$ and LD$_{100}$ of compounds N°. 1, 2, 3, 4a, 4b and 5b are grouped together in the following table:

TABLE 1

| Compound N° | Limit dose 0 | Limit dose 100 |
|---|---|---|
| 1 | 800 mg/kg | >800 mg/kg |
| 2 | 200 mg/kg | 400 mg/kg |
| 3 | 100 mg/kg | 400 mg/kg |
| 4a | 400 mg/kg | 800 mg/kg |
| 4b | 200 mg/kg | 800 mg/kg |
| 5b | 200 mg/kg | >400 mg/kg |

II. Analgesic activity

1. Hot-plate test in the mouse

This consists of measuring the time for appearance of a nociceptive reaction to a thermoalgesic stimulus in the mouse.

The animal is placed on a metal plate maintained at a constant temperature of 56° C. It reacts by licking its back paws in a time ranging from 4 to 12 seconds. After administration of an analgesic, the time taken for the reflex to appear is longer: an increase in threshold is obtained.

The maximal exposure time is limited to 30 seconds, taken as an arbitrary lapse of time indicating total analgesia.

The significant increase in time for the appearance of a reflex in animals having received a per os dose of compounds N°. 1, 2, 3, 4a, 4b and 5b in hydrochlorate form is marked by a (+) in table 2, depending on whether significance is reported or not:

TABLE 2

| Compound N° | Dose administered | Route | Significant increase in the time for appearance of a reflex | Degree of significance |
|---|---|---|---|---|
| 1 | 100 mg/kg | Per os | (+) | p <0.05 |
| 2 | 30 mg/kg | Per os | (+) | p <0.05 |
| 3 | 20 mg/kg | Per os | non significative | |
| 4a | 70 mg/kg | Per os | (+) | p <0.001 |
| 4b | 30 mg/kg | Per os | (+) | p <0.01 |
| 5b | 30 mg/kg | Per os | (+) | p <0.05 |

Of the two diastereoisomers N°. 4a and 4b, the most active is compound N°. 4a and the toxicity of these two compounds is low, particularly that of compound N°. 4a.

2. Abdominal spasms test in the mouse

This study, used for the selection of analgesics, consists of investigating the possible protection against abdominal spasms and/or contortions provoked, in the mouse, by intraperitoneal injection of acetic acid.

The significant decrease in the number of spasms in animals having received a per os dose of compounds N°. 1, 2, 3, 4a, 4b and 5b in hydrochlorate form is marked by a (+) in table 3, depending on whether significance is reported or not:

TABLE 3

| Compound N° | Dose administered | Route | Significant decrease in the number of cramps | Degree of significance |
|---|---|---|---|---|
| 1 | 100 mg/kg | Per os | non significative | |
| 2 | 30 mg/kg | Per os | non significative | |
| 3 | 20 mg/kg | Per os | non significative | |
| 4a | 70 mg/kg | Per os | (+) | $p < 0.001$ |
| 4b | 30 mg/kg | Per os | (+) | $p < 0.01$ |
| 5b | 30 mg/kg | Per os | non significative | |

III. Antidepressant activity

1. Desperation test in the mouse

A depressive state can be induced in the mouse by forcing it to swim in a narrow, cylindrical container from which it cannot escape. After a brief period of intense activity, the mouse adopts a characteristic immobile position that is easily identifiable.

Antidepressants reduce this immobility.

The significant reduction in immobility of animals having received a per os dose of compounds N°. 1, 2, 3, 4a, 4b and 5b in hydrochlorate form is marked by a (+) in table 4, depending on whether significance is reported or not:

TABLE 4

| Compound N° | Dose administered | Route | Significant reduction in immobility | Degree of significance |
|---|---|---|---|---|
| 1 | 100 mg/kg | PO | non significative | |
| 2 | 30 mg/kg | PO | non significative | |
| 3 | 20 mg/kg | PO | + | $p < 0.05$ |
| 4a | 70 mg/kg | PO | + | $p < 0.01$ |
| 4a | 64 mg/kg | IP | + | $p < 0.01$ |
| 4b | 30 mg/kg | PO | non significative | |
| 4b | 30 mg/kg | IP | + | $p < 0.05$ |
| 5b | 30 mg/kg | PO | non significative | |

2. Escape test in the mouse

This exploration test in the mouse consists of measuring, in a special enclosure, the time after which the first exploration begins and the total number of explorations throughout the duration of the test. Oral administration of a dose ranging from 20 mg/kg to 100 mg/kg of compounds N°. 1, 2, 3, 4a, 4b and 5b in hydrochlorate form does not lead to any modification in the behaviour of animals.

3. Openwork-floor test in the mouse and study of reflexes

This test consists of investigating an effect on the central nervous system by studying exploration and response to different reflexes in the mouse: corneal, auricular, straightening up, tensing up and clinging.

Oral administration of a dose ranging from 20 mg/kg to 100 mg/kg of compounds N°. 1, 2, 3, 4a, 4b and 5b in hydrochlorate form does not have any effect on the central nervous system of animals.

Furthermore, administration of compounds 4a and 4b, which show a significant antidepressant effect, does not lead to any modification in the motricity of animals.

The results of the pharmacological tests reported hereinabove allow therapeutic application of the compounds of the invention and pharmaceutically acceptable acid addition salts thereof to be considered, namely as analgesics and antidepressants.

The invention thus also relates to pharmaceutical compositions containing a compound of formula I or a pharmaceutically acceptable acid addition salt thereof, associated with a pharmaceutically acceptable agent or excipient.

The drugs can be presented, for example, in the form of tablets, vials for injection, suppositories or capsules at doses ranging from 10 mg to 500 mg per dose.

What is claimed is:

1. Compounds of the formula:

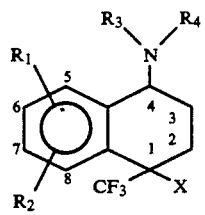

or an acid addition salt thereof, wherein:

X represents an aromatic nucleus which is phenyl, napthyl, or α or β thienyl, unsubstituted or carrying one or two substituents selected from the group consisting of halogeno, hydroxy, $C_1$ to $C_8$ alkoxy or trifluoromethyl;

$R_1$ represents a hydrogen atom or a halogen, a hydroxy group, a $C_1$ to $C_8$ alkoxy group, in one of positions 5, 6 or 7, or a methylenedioxy group in positions 5 and 6 or 6 and 7;

$R_2$ represents a hydrogen atom or a halogen, a hydroxy group, a $C_1$ to $C_8$ alkoxy group in one of the other positions 5, 6 or 7, and $R_3$ and $R_4$ together with the nitrogen atom to which they are linked form a group of the formula:

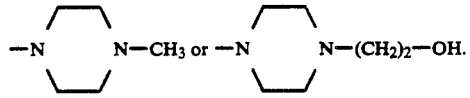

2. Compounds according to claim 1 wherein X represents a phenyl ring unsubstituted or carrying one or two substituents selected from the group consisting of halogeno, hydroxy, $C_1$ to $C_8$ alkoxy, and trifluoromethyl.

3. Compounds according to claim 2 wherein in formula I, X represents a phenyl ring substituted with one or two halogen atoms.

4. Compounds according to claim 1 wherein X represents a phenyl ring carrying one or two chlorine or fluorine atoms, $R_1$ represents a methoxy group or a chlorine atom, $R_2$ represents a hydrogen atom and $R_3$ and $R_4$ together with the nitrogen atom to which they are linked form a group of formula

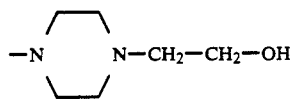

5. Compounds according to claim 1 wherein X represents a phenyl ring carrying one or two chlorine or fluorine atoms, $R_1$ represents a methylene-dioxy group fixed in position 6 and 7, $R_2$ represents a hydrogen atom, and $R_3$ and $R_4$ together with the nitrogen atom to which they are linked form a group of formula

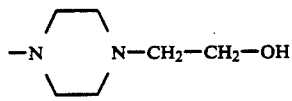

6. Compound conforming with any one of claims 1, 2, 3, 4 or 5 which is an acid addition salt.

7. Pharmaceutical composition containing a compound according to any one of claims 1, 2, 3, 4 or 5, and optionally a pharmaceutically acceptable agent or excipient.

8. A pharmaceutical composition containing a compound according to claim 6 and optionally a pharmaceutically acceptable agent or excipient.

9. Pharmaceutical composition conforming to claim 7, for the treatment of pain.

10. Pharmaceutical composition conforming to claim 7, for treatment of depressive states.

11. Compounds according to claim 1, 2 or 3, wherein $R_1$ and $R_2$ each represent a hydrogen atom, $R_3$ and $R_4$ together with the nitrogen atom to which they are linked form a group of the formula

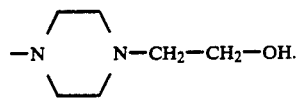

12. Compound conforming with claim 11, which is an acid addition salt.

13. A pharmaceutical composition containing a compound according to claim 11 and optionally a pharmaceutically acceptable agent or excipient.

14. Pharmaceutical composition conforming to claim 13, for treatment of pain.

15. Pharmaceutical composition conforming to claim 13, for treatment of depressive states.

16. Pharmaceutical composition conforming to claim 8, for treatment of pain.

17. Pharmaceutical composition conforming to claim 8, for treatment of depressive states.

* * * * *